US012797446B2

(12) United States Patent
Han et al.

(10) Patent No.: US 12,797,446 B2
(45) Date of Patent: Nov. 17, 2026

(54) DOSING REGIMEN

(71) Applicants: VIIV HEALTHCARE UK (NO. 7) LIMITED, Stevenage (GB); Halozyme, Inc., San Diego, CA (US)

(72) Inventors: Kelong Han, Collegeville, PA (US); Andrew Weber, Durham, NC (US); Michael James Labarre, San Diego, CA (US); Jessica Brehm, Research Triangle Park, NC (US); Nima Akhavein, Collegeville, PA (US); Emile Velthuisen, Research Triangle Park, NC (US)

(73) Assignees: VIIV HEALTHCARE UK (NO. 7) LIMITED (GB); Halozyme Inc, San Diego, CA (US)

( * ) Notice: Subject to any disclaimer, the term of this patent is extended or adjusted under 35 U.S.C. 154(b) by 521 days.

(21) Appl. No.: 18/332,893

(22) Filed: Jun. 12, 2023

(65) Prior Publication Data

US 2023/0405095 A1 Dec. 21, 2023

Related U.S. Application Data

(60) Provisional application No. 63/366,150, filed on Jun. 10, 2022.

(51) Int. Cl.
*A61K 38/47* (2006.01)
*A61K 31/4985* (2006.01)
*A61P 31/18* (2006.01)
*A61M 5/19* (2006.01)

(52) U.S. Cl.
CPC .......... *A61K 38/47* (2013.01); *A61K 31/4985* (2013.01); *A61P 31/18* (2018.01); *C12Y 302/01035* (2013.01); *A61M 5/19* (2013.01)

(58) Field of Classification Search
None
See application file for complete search history.

(56) References Cited

FOREIGN PATENT DOCUMENTS

| | | | | |
|---|---|---|---|---|
| EP | 2907504 A1 * | 8/2015 | .............. | A61P 43/00 |
| WO | WO-2022109555 A1 * | 5/2022 | ............. | A61K 47/10 |

* cited by examiner

*Primary Examiner* — Michelle F. Paguio Frising
(74) *Attorney, Agent, or Firm* — William B. Stauffer

(57) ABSTRACT

Provided are combination dosing regimens comprising administering cabotegravir and hyaluronidase. Combinations and compositions containing the cabotegravir and hyaluronidase are provided. The dosing regimens and combinations are for treating or preventing Human Immunodeficiency Virus (HIV) infection.

2 Claims, 1 Drawing Sheet

Specification includes a Sequence Listing.

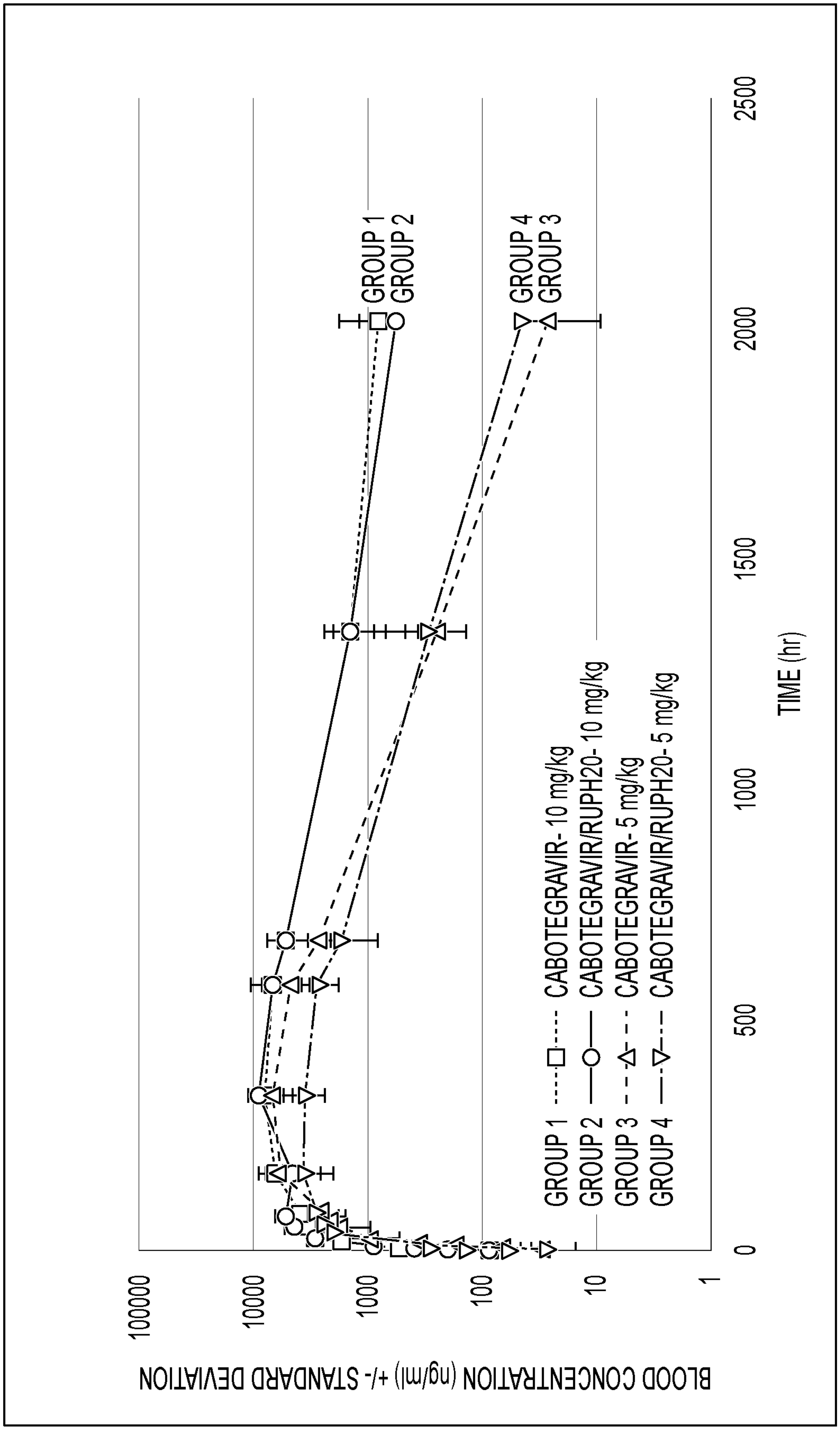
BLOOD CONCENTRATION (ng/ml) +/- STANDARD DEVIATION
100000
10000
1000
100
10
1
0
500
1000
1500
2000
2500
TIME (hr)
GROUP 1 CABOTEGRAVIR- 10 mg/kg
GROUP 2 CABOTEGRAVIR/RUPH20- 10 mg/kg
GROUP 3 CABOTEGRAVIR- 5 mg/kg
GROUP 4 CABOTEGRAVIR/RUPH20- 5 mg/kg
GROUP 1
GROUP 2
GROUP 4
GROUP 3

SEQUENCE LISTING

```
Sequence total quantity: 2
SEQ ID NO: 1           moltype = AA  length = 509
FEATURE                Location/Qualifiers
source                 1..509
                       mol_type = protein
                       note = precursor human PH20
                       organism = Homo sapiens
SEQUENCE: 1
MGVLKFKHIF FRSFVKSSGV SQIVFTFLLI PCCLTLNFRA PPVIPNVPFL WAWNAPSEFC  60
LGKFDEPLDM SLFSFIGSPR INATGQGVTI FYVDRLGYYP YIDSITGVTV NGGIPQKISL  120
QDHLDKAKKD ITFYMPVDNL GMAVIDWEEW RPTWARNWKP KDVYKNRSIE LVQQQNVQLS  180
LTEATEKAKQ EFEKAGKDFL VETIKLGKLL RPNHLWGYYL FPDCYNHHYK KPGYNGSCFN  240
VEIKRNDDLS WLWNESTALY PSIYLNTQQS PVAATLYVRN RVREAIRVSK IPDAKSPLPV  300
FAYTRIVFTD QVLKFLSQDE LVYTFGETVA LGASGIVIWG TLSIMRSMKS CLLLDNYMET  360
ILNPYIINVT LAAKMCSQVL CQEQGVCIRK NWNSSDYLHL NPDNFAIQLE KGGKFTVRGK  420
PTLEDLEQFS EKFYCSCYST LSCKEKADVK DTDAVDVCIA DGVCIDAFLK PPMETEEPQI  480
FYNASPSTLS ATMFIVSILF LIISSVASL                                   509

SEQ ID NO: 2           moltype = AA  length = 431
FEATURE                Location/Qualifiers
source                 1..431
                       mol_type = protein
                       organism = synthetic construct
SEQUENCE: 2
FRAPPVIPNV PFLWAWNAPS EFCLGKFDEP LDMSLFSFIG SPRINATGQG VTIFYVDRLG  60
YYPYIDSITG VTVNGGIPQK ISLQDHLDKA KKDITFYMPV DNLGMAVIDW EEWRPTWARN  120
WKPKDVYKNR SIELVQQQNV QLSLTEATEK AKQEFEKAGK DFLVETIKLG KLLRPNHLWG  180
YYLFPDCYNH HYKKPGYNGS CFNVEIKRND DLSWLWNEST ALYPSIYLNT QQSPVAATLY  240
VRNRVREAIR VSKIPDAKSP LPVFAYTRIV FTDQVLKFLS QDELVYTFGE TVALGASGIV  300
IWGSWENTRT KESCQAIKEY MDTTLNPYII NVTLAAKMCS QVLCQEQGVC IRKNWNSSDY  360
LHLNPDNFAI QLEKGGKFTV RGKPTLEDLE QFSEKFYCSC YSTLSCKEKA DVKDTDAVDV  420
CIADGVCIDA F                                                      431
```

DOSING REGIMEN

RELATED APPLICATIONS

Benefit of priority is claims to U.S. provisional application Ser. No. 63/366,150, filed on Jun. 10, 2022, entitled “Dosing Regimen,” to inventors Kelong Han, Andrew Weber, and Michael James LaBarre, and Applicant ViiV Healthcare UK (No. 7) Limited.

FIELD OF THE INVENTION

The inventions herein relate to combination dosing regimen comprising administering cabotegravir and hyaluronidase. Provided are dosing regimens and combinations for treating or preventing Human Immunodeficiency Virus (HIV) infection.

INCORPORATION BY REFERENCE OF SEQUENCE LISTING PROVIDED ELECTRONICALLY

An electronic version of the Sequence Listing is filed herewith, the contents of which are incorporated by reference in their entirety. The electronic file was created on Jun. 12, 2023, is 3,844 bytes in size, and is titled 70175US02 Seq List XML 12 Jun. 2023.xml.

BACKGROUND

It is estimated that approximately 38 million people are currently living with HIV or acquired immunodeficiency syndrome (AIDS) and that the worldwide epidemic continues to grow at a rate of 1.5 million new infections and cause 0.68 million deaths per year (UNAIDS, 2021). Patients with HIV infection commonly undergo complex treatment regimens that involve taking multiple pills at regular intervals each day. Patient non-compliance is a known problem accompanying these complex HIV treatment regimens and can lead to the emergence of multiple-drug resistant strains of HIV. Patient surveys have shown that the majority of patients would prefer to receive a long-acting injectable regimen at fewer intervals rather than taking oral daily tablets.

Cabotegravir, an HIV integrase inhibitor is approved in the USA and other countries and is dosed together with rilpivirine, a reverse transcriptase inhibitor, to treat HIV infection in people who are virally suppressed. Cabotegravir is dosed once monthly or once every two months via intramuscular gluteal injections. Cabotegravir also is approved by the FDA for pre-exposure prophylaxis (PrEP) to reduce the risk of sexually acquired HIV-1 infection. For PrEP, cabotegravir is given as a gluteal intramuscular injection every 2 months. Cabotegravir is the only marketed long-acting treatment for and long-acting prevention against HIV infection.

A safety concern when treating patients with injectable suspensions is injection site reactions. Combining cabotegravir with other drug products can alter the injection site reaction profile of cabotegravir. Combining cabotegravir with other drug products also may alter the pharmacokinetic (pK) profile of cabotegravir.

Long-acting injectable treatments are limited by patient experience and side effects. Achieving an injectable suspension with a high concentration of drug in order to dose less frequently and overcome the non-compliance problem with HIV treatment regimens, whilst maintaining product stability, avoiding drug-drug interactions and avoiding patient side effects is desirable.

There is a need in the art for a treatment and prevention for HIV infection that can be dosed at fewer intervals without increasing injection site reactions.

SUMMARY

Provided are combination dosing regimens, comprising administering hyaluronidase; and administering a suspension of cabotegravir. Also provided are methods of treating or preventing human immunodeficiency virus (HIV) infection, comprising administering to a patient in need of treatment or prevention the combination dosing regimen as described herein. Provided are combinations and kits, comprising a composition comprising a soluble hyaluronidase; and a suspension comprising cabotegravir.

The combination dosing regimens and methods of treatment are advantageous. Hyaluronidase previously has been co-administered with biologics but has not been marketed as a combination with a small molecule, and particularly not with long-acting small molecule. Soluble hyaluronidase can be administered with suspensions of the anti-viral cabotegravir to allow a larger amount of cabotegravir to be administered to a patient at in a single dose that the amounts of cabotegravir administered alone or administered in combination with another anti-viral product. Thus, methods, regimens, and combinations provided herein can be administered less frequently.

BRIEF DESCRIPTION OF DRAWING

The FIGURE depicts mean blood concentration of cabotegravir vs time following a single subcutaneous administration of 5 and 10 mg/kg with and without co-administration of rHuPH20 in male Sprague-Dawley rats.

DETAILED DESCRIPTION

A. Definitions

Unless defined otherwise, all technical and scientific terms used herein have the same meaning as is commonly understood by one of skill in the art to which the invention(s) belong. All patents, patent applications, published applications and publications, GenBank® sequences, databases, websites and other published materials referred to throughout the entire disclosure herein, unless noted otherwise, are incorporated by reference in their entirety. If there are a plurality of definitions for terms herein, those in this section prevail. Where reference is made to a URL or other such identifier or address, it is understood that such identifiers can change and particular information on the internet can come and go, but equivalent information can be found by searching the internet. Reference thereto evidences the availability and public dissemination of such information.

As used herein the term ‘combination dosing regimen’ refers to at least two components administered together to a patient.

As used herein, the term ‘treatment’ or ‘treating’ refers to alleviating the specified condition, eliminating or reducing the symptoms of the condition, slowing or eliminating the progression, invasion, or spread of the condition and reducing or delaying the reoccurrence of the condition in a previously afflicted subject.

As used herein, the term 'prevention' or 'preventing' refers to precluding developing a disease, disorder, or condition or reducing the risk of developing the disease, disorder, or condition or reducing the symptoms thereof.

As used herein the term 'injection site reaction' means side effects at or near the spot where the infusion/injection was received. This includes pain or discomfort, redness, swelling, itching, bruising, lumps, infection complications (cellulitis or abscess), and irritation.

As used herein, a soluble hyaluronidase is a hyaluronidase of form thereof that is not GPI anchored, and that is soluble under physiological conditions and is secreted upon expression. Hyaluronidases, such as ovine and bovine hyaluronidases occur as soluble hyaluronidases. Human PH20 hyaluronidase does not occur as a soluble hyaluronidase. It is known in the art that removal of all or a part of the GPI anchor results in soluble forms.

As used herein the term 'rHuPH20' refers to the soluble hyaluronidase composition produced upon expression in a mammalian cell, such as a CHO cell, or other cell that effects glycosylation, of nucleic acid encoding residues 36-482 of SEQ ID NO:1. For expression in cells the encoding nucleic acid is linked to the native (residues 1-35 of SEQ ID NO:1) or a heterologous signal sequence for trafficking and secretion of the encoded polypeptides. The resulting secreted soluble glycoprotein is a heterogeneous mixture of polypeptides, including polypeptides that terminate at residues 479, 480, 481, and 482, and are composed of residues 36-479, 36-480, 36-481, and 36-482 with reference to SEQ ID NO:1. Shorter C-terminally truncated forms also may be included.

As used herein, "combination therapy" refers to a treatment in which a subject if given two or more therapeutic agents, such as at least two or at least three therapeutic agents, for treating a single disease.

As used herein, "hyaluronidase activity" refers to the ability to enzymatically catalyse the cleavage of hyaluronic acid. The United States Pharmacopeia (USP) XXII assay for hyaluronidase determines hyaluronidase activity indirectly by measuring the amount of higher molecular weight hyaluronic acid, or hyaluronan, (HA) substrate remaining after the enzyme is allowed to react with the HA for 30 min at 37° C. (USP XXII-NF XVII (1990) 644-645 United States Pharmacopeia Convention, Inc, Rockville, MD). A Reference Standard solution can be used in an assay to ascertain the relative activity, in units, of any hyaluronidase. In vitro assays to determine the hyaluronidase activity of hyaluronidases, such as PH20, including soluble PH20 and esPH20, are known in the art and described herein. Exemplary assays include the micro turbidity assay that measures cleavage of hyaluronic acid by hyaluronidase indirectly by detecting the insoluble precipitate formed when the uncleaved hyaluronic acid binds with serum albumin and the biotinylated-hyaluronic acid assay that measures the cleavage of hyaluronic acid indirectly by detecting the remaining biotinylated-hyaluronic acid non-covalently bound to microtiter plate wells with a streptavidin-horseradish peroxidase conjugate and a chromogenic substrate. Reference Standards can be used, for example, to generate a standard curve to determine the activity in Units of the hyaluronidase being tested.

As used herein, specific activity refers to Units of activity per mg protein. The milligrams of hyaluronidase is defined by the absorption of a solution of at 280 nm assuming a molar extinction coefficient of approximately 1.7, in units of M−1 cm−1.

As used herein, "neutral active" refers to the ability of a PH20 polypeptide to enzymatically catalyse the cleavage of hyaluronic acid at neutral pH (e.g., at or about pH 7.0).

As used herein, a "GPI-anchor attachment signal sequence" is a C-terminal sequence of amino acids that directs addition of a preformed GPI-anchor to the polypeptide within the lumen of the ER. GPI-anchor attachment signal sequences are present in the precursor polypeptides of GPI-anchored polypeptides, such as GPI-anchored PH20 polypeptides. The C-terminal GPI-anchor attachment signal sequence typically contains a predominantly hydrophobic region of 8-20 amino acids, preceded by a hydrophilic spacer region of 8-12 amino acids, immediately downstream of the w-site, or site of GPI-anchor attachment. GPI-anchor attachment signal sequences can be identified using methods well known in the art, such as but not limited to, in silico methods and algorithms (see, e.g., Udenfriend et al. (1995) *Methods Enzymol.* 250:571-582, Eisenhaber et al., (1999) *J. Biol. Chem.* 292: 741-758, Fankhauser et al., (2005) *Bioinformatics* 21:1846-1852, Omaetxebarria et al., (2007) *Proteomics* 7:1951-1960, Pierleoni et al., (2008) *BMC Bioinformatics* 9:392), including those that are readily available on bioinformatic websites, such as the ExPASy Proteomics tools site (e.g., the World Wide Web site expasy.ch/tools/).

As used herein, sequence identity refers to the relatedness between or among polypeptides among nucleic acid molecules. Sequence identity can be assessed by aligning two sequences and counting the number of differences between the aligned portion and the sequence to which it is compared. Whether any two molecules have nucleotide sequences or amino acid sequences that are at least 60%, 70%, 80%, 85%, 90%, 95%, 96%, 97%, 98% or 99% "identical" or "homologous" can be determined using known computer algorithms such as the "FASTA" program, using for example, the default parameters as in Pearson et al. (1988) *Proc. Natl. Acad. Sci. USA* 85:2444 (other programs include the GCG program package (Devereux, J., et al., *Nucleic Acids Research* 12(I):387 (1984)), BLASTP, BLASTN, FASTA (Altschul, S. F., et al., *J Mol Biol* 215:403 (1990)); Guide to Huge Computers, Martin J. Bishop, ed., Academic Press, San Diego, 1994, and Carrillo et al. (1988) *SIAM J Applied Math* 48:1073). For example, the BLAST function of the National Center for Biotechnology Information database can be used to determine identity. Other commercially or publicly available programs include, DNAStar "MegAlign" program (Madison, WI) and the University of Wisconsin Genetics Computer Group (UWG) "Gap" program (Madison WI). Percent homology or identity of proteins and/or nucleic acid molecules can be determined, for example, by comparing sequence information using a GAP computer program (e.g., Needleman et al. (1970) *J. Mol. Biol.* 48:443, as revised by Smith and Waterman ((1981) *Adv. Appl. Math.* 2:482). Briefly, the GAP program defines similarity as the number of aligned symbols (i.e., nucleotides or amino acids), which are similar, divided by the total number of symbols in the shorter of the two sequences. Default parameters for the GAP program can include: (1) a unary comparison matrix (containing a value of 1 for identities and 0 for non-identities) and the weighted comparison matrix of Gribskov et al. (1986) *Nucl. Acids Res.* 14:6745, as described by Schwartz and Dayhoff, eds., ATLAS OF PROTEIN SEQUENCE AND STRUCTURE, National Biomedical Research Foundation, pp. 353-358 (1979); (2) a penalty of 3.0 for each gap and an additional 0.10 penalty for each symbol in each gap; and (3) no penalty for end gaps.

Therefore, as used herein, the term "identity" or "homology" represents a comparison between a test and a reference polypeptide or polynucleotide.

As used herein, the term at least "90% identical to" refers to percent identities from 90 to 99.99 relative to the reference nucleic acid or amino acid sequence of the polypeptide. Identity at a level of 90% or more is indicative of the fact that, assuming for exemplification purposes a test and reference polypeptide length of 100 amino acids are compared. No more than 10% (i.e., 10 out of 100) of the amino acids in the test polypeptide differs from that of the reference polypeptide. Similar comparisons can be made between test and reference polynucleotides. Such differences can be represented as point mutations randomly distributed over the entire length of a polypeptide or they can be clustered in one or more locations of varying length up to the maximum allowable, e.g. 10/100 amino acid difference (approximately 90% identity). Differences are defined as nucleic acid or amino acid substitutions, insertions or deletions. At the level of homologies or identities above about 85-90%, the result should be independent of the program and gap parameters set; such high levels of identity can be assessed readily, often by manual alignment without relying on software.

As used herein, an aligned sequence refers to the use of homology (similarity and/or identity) to align corresponding positions in a sequence of nucleotides or amino acids. Typically, two or more sequences that are related by 50% or more identity are aligned. An aligned set of sequences refers to 2 or more sequences that are aligned at corresponding positions and can include aligning sequences derived from RNAs, such as ESTs and other cDNAs, aligned with genomic DNA sequence.

As used herein, "denaturing condition" or "denaturation condition" refers to any condition or agent that, when exposed to a protein, affects or influences the degradation or denaturation of the protein, generally as a result of a loss or partial loss of the tertiary or secondary structure of the protein. Denaturing conditions can result in effects such as loss or reduction in activity, loss or reduction of solubility, aggregation and/or crystallization.

As used herein, "resistance to a denaturation condition" refers to any amount of decreased reduction or elimination of a property or activity of the protein associated with or caused by denaturation. For example, denaturation is associated with or causes increased crystallization or aggregation, reduced solubility or decreased activity. Hence, resistance to denaturation means that the protein exhibits decreased aggregation or crystallization, increased solubility or increased or greater activity (e.g., hyaluronidase activity) when exposed to a denaturing condition compared to a reference protein (e.g., unmodified enzyme).

As used herein, stability of a modified PH20 hyaluronidase means that it exhibits resistance to denaturation caused by a denaturation condition or denaturing agent.

For clarity of disclosure, and not by way of limitation, the detailed description is divided into the subsections that follow.

B. Overview

Provided are combination dosing regimens, comprising administering a hyaluronidase; and administering a suspension of cabotegravir. The agents in the dosing regimens can be administered sequentially, intermittently, serially, in the same composition, and/or in other combinations of the agents. The combination dosing regimens described herein are dosing regimens suitable to be provided to a patient in order to treat or prevent HIV infection.

In an embodiment of the combination dosing regimens provided are dosing regimens suitable for treating HIV infection. In an alternative embodiment, the combination dosing regimen provided herein is for preventing HIV infection, including reducing the risk of being infected with HIV infection. The combination dosing regimen is administered to a patient in need of treatment for HIV infection or a person in need of HIV prevention.

In embodiments herein, provided are combination dosing regimens in which cabotegravir and a soluble hyaluronidase are administered.

C. Cabotegravir

Cabotegravir (N-((2,4-Difluorophenyl)methyl)-6-hydroxy-3-methyl-5,7-dioxo-2,3,5,7,11,11a hexahydro(1,3) oxazolo(3,2-a)pyrido(1,2-d)pyrazine-8-carboxamide) is described in U.S. Pat. No. 8,129,385 (see e.g., Z-1, which example, as all referenced material, is incorporated herein by reference). Cabotegravir is an integrase strand transfer inhibitor (INSTI) that exhibits subnanomolar potency and antiviral activity against a broad range of HIV-1 strains. Cabotegravir has exhibited acceptable safety and tolerability profiles, a long half-life, and few drug-drug interactions. Cabotegravir has been demonstrated to be efficacious in treatment and prevention of HIV in oral and in parenteral dosage forms. Cabotegravir has been approved by the FDA as CABENUVA®, a long-acting injectable for the treatment of HIV infection, and as APRETUDE®, a long-acting injectable for the prevention of HIV infection. Cabotegravir (CAB) is represented by formula (I):

(I)

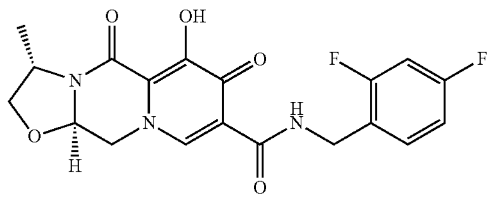

CAB is approved for the treatment of patients with HIV-1, as a long-acting (LA) intramuscular (IM) injection (200 mg/mL), co-administered with rilpivirine (RPV) (300 mg/mL) IM. This two-drug IM regimen of CAB and RPV is administered once-monthly or every 2 months for the treatment of HIV-1 infection in adults and adolescents 12 years of age and older and weighing at least 35 kg. Oral CAB (30 mg), co-administered with oral RPV (25 mg), also is used for optional oral lead-in and for a brief period of oral bridging when long-acting therapy is not available.

Long-acting treatment advantages compared to daily oral regimens, including infrequent dosing to decrease the daily reminder of HIV infection associated with oral antiretroviral therapy, reduced stigma, better compliance. As the number of individuals being treated with LA therapy increases, there is an impact on clinic resources. A goal herein is to increase dose intervals and/or provide for self-administration. Regimens and formulations provided herein allow self-administration by SC injection and can provide for longer dosing intervals. The regimens and formulations provided herein also can lengthen the dose interval for treatment for HIV prevention.

In embodiments herein, cabotegravir is provided in suspensions. The suspension includes any suitable suspension of cabotegravir, such as those exemplified. Combinations and treatment regimens are provided herein in which cabotegravir is administered in combination with a soluble hyaluronidase.

D. Soluble Hyaluronidases

Soluble hyaluronidases include any that, upon expression, are secreted from a cell and exist in soluble form. Such soluble hyaluronidases include, for example, but are not limited to, bacterial soluble hyaluronidases, non-human soluble hyaluronidases, such as bovine PH20 and ovine PH20, human soluble PH20, and variants thereof. Generally soluble forms of PH20 are produced using protein expression systems that facilitate correct N-glycosylation to ensure the polypeptide retains activity, since glycosylation is important for the catalytic activity and stability of hyaluronidases. Such cells include, for example Chinese Hamster Ovary (CHO) cells (e.g., DG44 CHO cells).

Soluble PH20 hyaluronidase is available and sold, for example, under the trademark ENHANZE®. ENHANZE® technology provides to a drug delivery technology, employing the soluble hyaluronidases to facilitate the delivery of injected drugs and fluids. When co-formulated with other drugs or administered with other drugs, the ENHANZE® technology reduces treatment burden for patients. It can allow for large volume subcutaneous injection with increased dispersion and absorption of co-administered therapies. ENHANZE® technology has been marketed with biologics; it has not, prior to the instant description, been used for delivery of specific small molecules, nor for delivery of therapeutics for treatment and/or prevention of HIV.

rHuPH20 refers to the composition produced upon expression in a cell, such as CHO cell, of nucleic acid encoding residues 36-482 of SEQ ID NO: 26, generally linked to the native or a heterologous signal sequence (residues 1-35 of SEQ ID NO: 26). rHuPH20 is produced by expression of a nucleic acid molecule, such as encoding amino acids 1-482 (set forth in SEQ ID NO: 26) in a mammalian cell. Translational processing removes the 35 amino acid signal sequence. As produced in the culture medium there is heterogeneity at the C-terminus such that the product, designated rHuPH20, includes a mixture of species that can include any one or more of the polypeptides 36-480, 36-481, and 36-482 of SEQ ID NO: 26, and some shorter polypeptides, in various abundance. rHuPH20 and forms of soluble hyaluronidase are produced in cells, such as CHO cells, for example DG44 CHO cells, that facilitate N-glycosylation. PH20 is a glycoprotein, and as known in the art, requires glycosylation retain activity. See, e.g., U.S. Pat. Nos. 8,927,249 and 9,284,543 (and PCT Publication No. WO 2010/077297), which describe the effects of glycosylation and partial glycosylation and elimination of glycosylation on the activity of soluble forms of PH20. These patents and publications also describe and exemplify I soluble C-terminally truncated forms of PH20.

1. Forms of Soluble Human PH20

Soluble hyaluronidases include bovine and ovine PH20, and recombinant and humanized forms thereof. Human PH20 in nature includes a GPI anchor and exists linked to sperm cells; it is not soluble. C-terminally-truncated forms thereof are soluble. Soluble forms of recombinant human PH20 have been produced and can be used in the compositions, combinations and methods described herein. Descriptions of and production of such soluble forms of PH20 are described, for example, in U.S. Pat. Nos. 7,767,429; 8,202,517; 8,431,380; 8,431,124; 8,450,470; 8,765,685; 8,772,246; 7,871,607; 7,846,431; 7,829,081; 8,105,586; 8,187,855; 8,257,699; 8,580,252; 9,677,061; and 9,677,062, each incorporated by reference herein. The soluble hyaluronidases, thus include forms of human PH20, which are neutral active hyaluronidases and which require glycosylation for activity.

SEQ ID NO: 1 sets forth the sequence of the precursor polypeptides; the mature PH20 polypeptide (residues 36-509); soluble forms also include those with amino acid truncations at the N-terminal, such as deletions of the first one, two, three, or fours residues, such that the resulting polypeptides have an N-terminus, for example, at residue 36, 37, 38, 39, or 40, and a C-terminus at a residue from 465 to 500, and variants thereof, including, but not limited to, variants discussed below, variants known in the art, and allelic variants.

Hyaluronidases for use in the compositions, combinations and methods herein are soluble neutral active hyaluronidases. Exemplary thereof are the soluble C-terminally truncated forms of mature human PH20. Soluble forms that have hyaluronidase activity, include but are not limited to, those that are truncated at residues from 465 to 500 of sequence ID No. 1, and that are, upon expression, secreted. Exemplary thereof are polypeptides that have sequence 36-465, 36-466, 36-467, 36-468, 36-469, 35-470, 36-471, 36-472, 36-474, 36-475, 36-476, 35-477, 36-478, 36-479, 36-480, 36-481, 36-482, 36-483 35-484, 36-485, 36-486, 36-487, 36-488, 36-489, 36-490, 35-491, 36-492, 36-493, 36-494, 36-495, 36-496, 36-497, 35-498, 36-499, and 36-500 of SEQ ID NO:1, as well as N-terminally truncated forms of each of the preceding that lack two to five residues at the N-terminus, such as for example 37-368, 38-468, and any others that exhibit hyaluronidase activity at neutral pH, such as pH in the range of 7.0-7.4.

Thus, such soluble forms include truncated forms of the mature form of human PH20 lacking all or a portion of the C-terminal GPI anchor, so long as the hyaluronidase is soluble and retains hyaluronidase activity. Soluble forms are secreted upon expression in mammalian cells, and are encoded with a signal sequence, such are residues 1-35 of SEQ ID NO. 1 or a heterologous signal sequence that is cleaved by the cell to effect secretion. Soluble forms are forms that, when expressed in a cell, lack the signal peptide. Also included among soluble hyaluronidases are variants of the soluble PH20 polypeptides that exhibit hyaluronidase activity. Variants include polypeptides having at least 60%, 70%, 80%, 85%, 90%, 91%, 92%, 93%, 94%, 95%, 96%, 97%, 98%, 99% or more sequence identity to any of the PH20 polypeptides 36-465, 36-466, 36-467, 36-468, 36-469, 35-470, 36-471, 36-472, 36-474, 36-475, 36-476, 35-477, 36-478, 36-479, 36-480, 36-481, 36-482, 36-483 35-484, 36-485, 36-486, 36-487, 36-488, 36-489, 36-490, 35-491, 36-492, 36-493, 36-494, 36-495, 36-496, 36-497, 35-498, 36-499, and 36-500 of SEQ ID NO:1. Amino acid variants include conservative and non-conservative insertions, or deletions, or replacements, and include the modifications, singly or combinations of the modifications detailed, for example, in U.S. Pat. No. 11,041,149 and International PCT publication No. WO 2013/102144. U.S. Pat. No. 11,041,149 and International PCT publication No. WO 2013/102144 describe a systematic analysis and results identifying the effects of amino acid modifications at each residue in PH20 to thereby provide a structure/function map of PH20; a skilled person can identify replacement residues and consequent alterations in properties and activities, such as for effecting increases in enzymatic activity, stability in denaturing conditions, and also residues whose replacement or deletion decreases or eliminates enzymatic activity.

It is understood that residues that are important or otherwise required for the activity of a hyaluronidase, such as any described above or known to those of skill in the art, are generally invariant and, except for possible conservative amino acid substitutions, cannot be changed. These include, for example, active site residues. For example, amino acid residues 111, 113 and 176 (corresponding to residues in the mature PH20 polypeptide) of a human PH20 polypeptide, or soluble form thereof, are generally invariant and are not altered. Other residues that confer glycosylation and formation of disulfide bonds required for proper folding also can be invariant.

The soluble human PH20 hyaluronidase is GPI-anchored and is rendered soluble by truncation at the C-terminus by removal of all or a part of the GPI anchor. Such truncation can remove all of the GPI anchor attachment sequence or can remove only some of the GPI anchor attachment sequence. The resulting polypeptide, however, is soluble. In instances where the soluble hyaluronidase retains a portion of the GPI anchor attachment signal sequence, 1, 2, 3, 4, 5, 6, 7 or more amino acid residues in the GPI anchor attachment signal sequence can be retained, provided the polypeptide is soluble. Polypeptides containing one or more amino acids of the GPI anchor are termed extended soluble hyaluronidases. One of skill in the art can determine whether a polypeptide is GPI-anchored using methods well known in the art. Such methods include, but are not limited to, using known algorithms to predict the presence and location of the GPI anchor attachment signal sequence and w-site, and performing solubility analyses before and after digestion with phosphatidylinositol-specific phospholipase C (PI-PLC) or D (PI-PLD).

Extended soluble hyaluronidases, which terminate for example, at residues 495, 496, 497, 498, 499, and 500, with reference to SEQ ID NO:1, such as those set forth in SEQ ID NOs: 61-66, can be produced by making C-terminal truncations to any naturally GPI-anchored hyaluronidase such that the resulting polypeptide is soluble and contains one or more amino acid residues from the GPI anchor attachment signal sequence (see, e.g., U.S. Pat. No. 8,927, 249). These include hyaluronidases that are neutral active, soluble, contain amino acid substitutions, and have at least 60%, 70%, 80%, 85%, 90%, 91%, 92%, 93%, 94%, 95% or more sequence identity to any of SEQ ID NOs: 61-66.

Typically, for use in the compositions, combinations and methods herein, a soluble human hyaluronidase, such as a soluble human PH20, is used, such as a PH20 and variants having, for example, at least 91% or 95% or 98% sequence identity thereto, including those with 1 to 5 N-terminal residues deleted. Hyaluronidases used in the regimens, combinations, compositions, and methods herein can be recombinantly produced or can be purified or partially purified from natural sources, such as, for example, from testes extracts. Methods for production of recombinant proteins, including recombinant hyaluronidases, are well known in the art.

Recombinant soluble forms of human PH20 have been generated and can be used in the compositions, combinations and methods provided herein. For example, with reference to SEQ ID NO: 1, which sets forth the sequence of full length precursor PH20, which includes a signal sequence (residues 1-35), soluble forms include, but are not limited to, C-terminal truncated polypeptides of human PH20 set forth in SEQ ID NO: 1 having a C-terminal amino acid residue 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498, 499 or 500 of the sequence of amino acids set forth in SEQ ID NO: 1, or polypeptides that exhibit at least 85%, 90%, 91%, 92%, 93%, 94%, 95%, 96%, 97%, 98%, 99%, or more sequence identity thereto, when aligned with the unmodified sequence of the soluble PH20, have activity at neutral pH, and are soluble (secreted into the medium when expressed in a mammalian cell). Soluble forms of human PH20 generally include those that contain amino acids 36-464 set forth in SEQ ID NO: 1 and terminate at any of residues, 465-500, and optionally include a 1-3 amino acid deletion at the N-terminus (i.e., lack residues 36, 36-37, or 36-38 of SEQ ID NO:1). For example, when expressed in mammalian cells, the 35 amino acid N-terminal signal sequence (residues 1-35 of SEQ ID NO:1) is cleaved during processing, and a soluble form of the protein is secreted. Thus, the mature soluble polypeptides include those that contain amino acids 36 to 467, 468, 469, 470, 471, 472, 473, 474, 475, 476, 477, 478, 479, 480, 481, 482, 483, and up to and including 500 of SEQ ID NO: 1. Exemplary of soluble hyaluronidases are soluble human PH20 polypeptides that are 442, 443, 444, 445, 446 or 447 amino acids in length, such as set forth those set forth above, and variants thereof that have, for example, at least 85%, 86%, 87%, 88%, 89%, 90%, 91%, 92%, 93%, 94%, 95%, 96%, 97%, 98% or 99% sequence identity thereto and retains hyaluronidase activity. The generation of such soluble forms of recombinant human PH20 are described, for example, in U.S. Pat. Nos. 7,767, 429; 8,202,517; 8,431,380; 8,431,124; 8,450,470; 8,765, 685; 8,772,246; 7,871,607; 7,846,431; 7,829,081; 8,105, 586; 8,187,855; 8,257,699; 8,580,252; 9,677,061; and 9,677,062.

Generally soluble forms of PH20 are produced using protein expression systems that facilitate correct N-glycosylation to ensure the polypeptide retains activity, since glycosylation is important for the catalytic activity and stability of hyaluronidases. Such cells include, for example Chinese Hamster Ovary (CHO) cells (e.g., DG44 CHO cells).

The composition that recombinantly produced from mammalian cells, such as CHO cells, has been referred to rHuPH20. It refers to the composition produced upon expression in a cell, such as CHO cell, of nucleic acid encoding residues 36-482 of SEQ ID NO: 1, generally linked to the native (residues 1-35 of SEQ ID NO: 1) or a heterologous signal sequence. rHuPH20 is produced by expression of a nucleic acid molecule, such as encoding amino acids 1-482 (set forth in SEQ ID NO: 1) or 36 to 482 with a heterologous signal sequence. Post translational processing removes the 35 amino acid signal sequence, resulting in polypeptide or a mixture of polypeptides, including those set forth in SEQ ID NOs: 3 and 44-49. As produced in the culture medium there is heterogeneity at the C-terminus such that the product, designated rHuPH20, includes a mixture of species that can include any one or more of SEQ ID NOs: 3 and 44-49 in various abundance. Generally, the soluble hyaluronidases, rHuPH20 is produced in cells that facilitate correct N-glycosylation to retain activity, such as CHO cells (e.g., DG44 CHO cells). Human soluble PH20 hyaluronidase requires glycosylation for activity. When produced recombinantly from a vector encoding residues 36-582, the most abundant species is the 446 amino acid polypeptides corresponding to residues 36-481 of SEQ ID NO: 1. The particular distribution of resulting polypeptides can depend upon the particular method of production. An exemplary method for production of high levels of PH20 is detailed, for example in U.S. Pat. Nos. 8,187,855 and 8,343,487.

2. Glycosylation of Hyaluronidases

Glycosylation, including N- and O-linked glycosylation, of some hyaluronidases, including the soluble PH20 hyaluronidases, can be important for their catalytic activity and stability. For some hyaluronidases, removal of N-linked glycosylation can result in near complete inactivation of the hyaluronidase activity. For such hyaluronidases, the presence of N-linked glycans can be important for generating an active enzyme.

N-linked oligosaccharides fall into several primary types (oligomannose, complex, hybrid, sulfated), all of which have (Man) 3-GlcNAc-GlcNAc-cores attached via the amide nitrogen of Asn residues that fall within -Asn-Xaa-Thr/Ser-sequences (where Xaa is not Pro). Glycosylation at an -Asn-Xaa-Cys-site has been reported for coagulation protein C. In some instances, a hyaluronidase, such as a PH20 hyaluronidase, can contain N-glycosidic and 0-glycosidic linkages. For example, PH20 has O-linked oligosaccharides as well as N-linked oligosaccharides. There are six potential N-linked glycosylation sites at N82, N166, N235, N254, N368, N393 of human PH20 exemplified in SEQ ID NO: 1.

3. Variants

As discussed above, variants of PH20 are known to those of skill in the art, or readily can be prepared in view of the skill and knowledge in the art. Variants include those with amino acid replacements, insertions, and deletions. Variants of the soluble PH20 polypeptides that have altered properties, such as increased stability and/or activity, have been produced. U.S. Pat. No. 9,447,401 and family members U.S. Pat. Nos. 10,865,400, 11,041,149 and 11,066,656 describe and provide a structure/function map of human PH20 detailing the effects of amino acid replacements at every residue in the catalytic domain of PH20. These patents provide about 7000 examples in which the effects of replacing each amino acid with 15 other amino acids on activity and stability were identified and described. By virtue of those patents, and earlier publications/patents, describing virtually all variants of soluble PH20 polypeptides are known in the art. A skilled person readily can prepare soluble hyaluronidases and variants thereof and know the properties of the resulting hyaluronidase.

Other variants also are known to those of skill in the art, and can be used in the combinations, regimens, and methods described herein. For example, see, International PCT Publication Nos. WO2020/022791 and WO2020197230A, which are incorporated by reference, and which describe modified PH20 polypeptides. These polypeptides, which include variants of the PH20 polypeptides that generally span residues 38-468, and include replacements, insertions, and deletions. The variants include for example one or more amino acid residues changes S343E, I344N, M345T, M348K, K349E, L353A, L354I, N356E, and I361T (with reference to SEQ ID NO:1), and others, including about 15 amino acid variations, and truncations at the N-terminus and C-terminus. Variants that contain such modifications and others are set forth in SEQ ID NOs: 60-115 of International PCT publication No. WO2020/022791. Exemplary of these polypeptides is the polypeptide of SEQ ID NO:99, therein, and reproduced below as SEQ ID NO:2. International PCT Publication No. WO2021/150079 provides variant PH20 polypeptides described as having increased stability relative to unmodified PH20, such as those in rHuPH20. These variant polypeptides have been shown to have PH20 activity and are described as having use for subcutaneous co-administration with other agents.

E. Regimens and Combinations

1. Regimens

Provided are regimens for administration of Cabotegravir in combination with a soluble hyaluronidase. The Cabotegravir generally is formulated as a suspension at concentrations and the hyaluronidase is provided as a composition containing an effective concentration of soluble hyaluronidase for delivery of an effective amount of hyaluronidase in about 0.5 mL to 10 mL, such as 1 mL to 5 mL, or 1 mL to 3 mL. The Cabotegravir and hyaluronidase can be administered separately or co-formulated for administration in a single composition. When administered separately, they can be administered in any order, but generally the hyaluronidase is administered first. The cabotegravir and/or hyaluronidase can be provided as separate compositions, such as suspension and solutions, or can be provided as a co-formulation.

As described herein, the hyaluronidase and cabotegravir can be administered together or sequentially or any other defined regimen. For example, in some embodiments, the hyaluronidase is administered to a patient before cabotegravir is administered i.e. in a first step hyaluronidase is administered to a patient; and in a second step cabotegravir is administered to a patient. In an embodiment cabotegravir is administered to the patient as soon as possible after hyaluronidase has been administered to the patient i.e. immediately after hyaluronidase has been administered to the patient.

In an embodiment, each of the hyaluronidase and cabotegravir can be administered to a patient via an injection. In an embodiment the hyaluronidase and cabotegravir each is administered subcutaneously. For example, the hyaluronidase and cabotegravir can be administered to a patient subcutaneously in the abdominal tissue. The hyaluronidase and cabotegravir can be administered separately or in the same composition.

It is shown and described herein that when cabotegravir is administered in combination with the hyaluronidase, dispersion of the co-injected drugs is enhanced. By depolymerizing hyaluronan, hyaluronidase temporarily facilitates dispersion by reducing the viscosity of interstices. The permeability barrier in these tissues is restored to pre-injection levels within 24 to 48 hours after injection of hyaluronidase. This allows for higher volumes in a single injection of cabotegravir to be administered to the patient.

When administered in separate compositions, the hyaluronidase and cabotegravir are injected as close to the same site as possible. For example, in an embodiment, hyaluronidase is first injected to a patient at a first injection site and subsequently the cabotegravir is injected at the same injection site or at an injection site as close to the first injection site as possible.

In an embodiment, the suspension of cabotegravir has a concentration of about 200 mg/mL of cabotegravir or about 400 mg/mL of cabotegravir. In an embodiment, the suspension of cabotegravir has a concentration of about 200 mg/mL of cabotegravir, for example 200 mg/mL of cabotegravir. Extended-release suspensions comprising 200 mg/mL of cabotegravir are described in WO 2012/037320, which is incorporated herein by reference. In an embodiment, the 200 mg/mL extended-release suspension of cabotegravir is as described in Example 1 of WO 2012/037320, such example, as all reference material, is incorporated herein by reference. The formulation described in this example is referred to herein as CAB200. In an alternative embodiment, the suspension of cabotegravir has a concentration of about 400 mg/mL of cabotegravir, for example 400 mg/mL of cabotegravir. Extended-release suspensions comprising 400 mg/mL of cabotegravir are described in WO 2021/16872, which is incorporated herein by reference. In an embodiment, the 400 mg/mL extended-release suspension of cabotegravir is as described in example 1 of WO 2021/16872, such example is incorporated herein by reference. The formulation described in this example is referred to herein as CAB400.

In accord with regimens and compositions provided herein, the hyaluronidase is administered in an amount suitable to allow a dose of from 800 mg to 4000 mg of cabotegravir to be administered to the patient. Exemplary ranges include, but are not limited to, an amount suitable to allow a dose of from 900 mg to 4000 mg of cabotegravir to be administered to the patient, or dose of at least 800 mg, 900 mg, 1000 mg, 1100 mg, 1200 mg, 1300 mg, 1400 mg, 1500 mg, 1600 mg, 1700 mg, 1800 mg, 1900 mg, 2000 mg, 2100 mg, 2200 mg, 2300 mg, 2400 mg, 2500 mg, 2600 mg, 2700 mg, 2800 mg, 2900 mg, 3000 mg, 3100 mg, 3200 mg, 3300 mg, 3400 mg, 3500 mg, 3600 mg, 3700 mg, 3800 mg, 3900 mg or 4000 mg or more to be administered to a patient. In other embodiments, the hyaluronidase is administered in an amount suitable to allow a dose of at least or at about 800 mg, 1600 mg, 2400 mg or 4000 mg of cabotegravir to be administered. It is understood that a skilled practitioner can determine a particular dose, which can depend upon various parameters include the mass of the patient, the age of the patient, and other conditions of the patient.

In an exemplary embodiment, a suspension of cabotegravir is administered at a dose of from 800 mg to 4000 mg, such as, but not limited to, a dose of from 900 mg to 2000 mg, such as for example, a dose of at least or at 800 mg, 900 mg, 1000 mg, 1100 mg, 1200 mg, 1300 mg, 1400 mg, 1500 mg, 1600 mg, 1700 mg, 1800 mg, 1900 mg, 2000 mg, 2100 mg, 2200 mg, 2300 mg, 2400 mg, 2500 mg, 2600 mg, 2700 mg, 2800 mg, 2900 mg, 3000 mg, 3100 mg, 3200 mg, 3300 mg, 3400 mg, 3500 mg, 3600 mg, 3700 mg, 3800 mg, 3900 mg or 4000 mg. Exemplary thereof the suspension of cabotegravir is administered at a dose of 800 mg, 1600 mg, 2400 mg or 4000 mg or in amounts in between such doses. For example, a suspension of cabotegravir is administered at a dose of about 800 mg, or at a dose of about 1600 mg, or at a dose of about 2400 mg, or at a dose of about 4000 mg.

Hyaluronidases have been used clinically since the 1950s. For example, rHuPH20, approved by the FDA in 2004, has been shown to be well tolerated in clinical evaluation of subcutaneous doses of up to 96,000 U, wherein U is USP units. For example, for purposes herein, hyaluronidase is administered at a dose of from 2000 to 15,000 U, such as, but not limited to from 5,000 to 15,000 U, such as 6,000 to 12,000 U, 8,000 to 12,000 U, such as at or about a dose of about 10,000 U, for example 10,000 U. The hyaluronidase is administered in volumes that range from at or about 0.5 mL to 10 mL, such as 1 mL to 5 mL, or at or about 1 mL to 3 mL injection, such as a 1 mL injection; the volume is a function of the specific activity of a particular formulation of the hyaluronidase. The particular amount depends upon a parameters understood by those of skill in the art. Co-administration of cabotegravir with hyaluronidase, as noted, allows for administration of a higher doses and larger volumes of cabotegravir potentially affording a longer interval between injections. This can increase the convenience of long-acting regimens and can result in better adherence to therapy and positively impact treatment outcomes and acceptability.

As discussed above, the combination of cabotegravir and hyaluronidase can allow less frequent dosing compared to administration of cabotegravir, or cabotegravir with other HIV agents, in dosing regimens that do not include a hyaluronidase. For example, in accord with the instant disclosure, hyaluronidase and cabotegravir are administered once every 3 months to once every year, such as once every 3 months, once every 4 months, once every 5 months or once every 6 months or other intervals that are longer than 3 months and less than 6 months, 9 months, or one year. In an exemplary regimen, hyaluronidase and cabotegravir are administered once every 3 months.

In one embodiment, combination dosing regimen is provided that comprises administering hyaluronidase; and a suspension of cabotegravir, wherein hyaluronidase is administered at a dose of from 4000 to 15,000 U; and cabotegravir is administered at a dose of from 800 mg to 4000 mg. Wherein the combination dosing regimen is administered once every 3 months to once every 6 months.

In another embodiment, provided a combination dosing regimen comprising administering hyaluronidase; and administering a suspension of cabotegravir, wherein hyaluronidase is administered at a dose of from 6000 to 12,000 U; and cabotegravir is administered at a dose of from 800 mg to 4000 mg. Wherein the combination dosing regimen is administered once every 3 months to once every 6 months.

In another embodiment, provided a combination dosing regimen comprising administering hyaluronidase; and administering a suspension of cabotegravir, wherein hyaluronidase is administered at a dose of 10,000 U; and cabotegravir is administered at a dose of from 800 mg to 4000 mg. In this regime the cabotegravir suspension has a concentration of 200 mg/mL, and the combination dosing regimen is administered once every 3 months.

The regimens provide herein are for treating or preventing human immunodeficiency virus (HIV) infection comprising administering to a patient in need of treatment or prevention a combination dosing regimen described herein. Prevention, as described herein, includes reducing the risk of infection. Hence in embodiments herein, provide are methods of treating human immunodeficiency virus (HIV) infection, the method comprising administering to a patient a combination dosing regimen described herein. In an alternative embodiment, provided is a method of preventing HIV infection, the method comprising administering to a human the combination dosing regimen described herein. In the first methods, the patient has been diagnosed with HIV; in the latter, the subject has not been diagnosed with HIV, but, generally is a subject at risk of exposure to HIV.

In a further aspect, the combination dosing regimens as described herein are for use in the treatment or prevention of HIV infection. In an embodiment, the combination dosing regimens described herein are for use in the treatment of HIV infection. In an alternative embodiment, the present invention provides the combination dosing regimen as described herein for use in the prevention of HIV infection.

2. Combinations and Compositions and Kits

Provided herein are compositions, combinations and kits. The combinations comprise a composition containing the hyaluronidase; and a composition that is suspension comprising cabotegravir. The compositions comprising the cabotegravir are formulated as suspensions in amounts for administering a dose of cabotegravir, such as in an amount that is 800 mg to 4000 mg, such as such as, but not limited to, a dose of from 900 mg to 2000 mg, such as for example, a dose of at least or at 800 mg, 900 mg, 1000 mg, 1100 mg, 1200 mg, 1300 mg, 1400 mg, 1500 mg, 1600 mg, 1700 mg, 1800 mg, 1900 mg, 2000 mg, 2100 mg, 2200 mg, 2300 mg, 2400 mg, 2500 mg, 2600 mg, 2700 mg, 2800 mg, 2900 mg, 3000 mg, 3100 mg, 3200 mg, 3300 mg, 3400 mg, 3500 mg, 3600 mg, 3700 mg, 3800 mg, 3900 mg or 4000 mg as detailed above. Each of the compositions can be formulated for single dosage or multiple dosage administration or for dilution as appropriate.

The hyaluronidase is formulated for administration of a dose from 2000 to 15,000 U, such as, but not limited to from 5,000 to 15,000 U, such as 6,000 to 12,000 U, 8,000 to 12,000 U, such as at or about a dose of about 10,000 U, for example 10,000 U. Compositions containing hyaluronidase for administration are well known, and generally are formulated at a pH of about 7 to about 7.4, in appropriate buffers, salts, stabilizers and surfactant as needed. See e.g., U.S. Pat. No. 7,767,429. Variants, as described herein, that are more stable in denaturing conditions, such as those described in U.S. Pat. No. 9,447,401 and family members and variants designed for increased activity and/or stability can be formulated. The hyaluronidase and cabotegravir can be co-formulated as suspensions or mixed prior to use for administration in a single composition. The compositions containing both are formulated to deliver an appropriate dose of each.

The combinations can contain the two compositions or the single co-formulations, and optionally instructions for use. The combinations can be packaged as kits. Exemplary combinations and kits can include a syringe or other container containing the hyaluronidase, and a syringe or other container containing the suspension of cabotegravir. Alternatively, the cabotegravir and hyaluronidase can be provided in a dual compartment container, such as a dual compartment syringe where the compositions are separated, such as by a membrane that can be punctured prior to administration. In these aspects, the hyaluronidase and cabotegravir are as described herein.

EXAMPLES

The following examples are included for illustrative purposes only and are not intended to limit the scope of the invention.

Example 1: Effect of rHuPH20 on the Pharmacokinetic Profile of Cabotegravir Following Subcutaneous Administration Cabotegravir (free acid) was supplied by the Department of Pharmaceutical Development, at GSK, Upper Providence (UP), as a wet bead milled suspension (WBM), of nominal 200 mg/mL active concentration, white to slightly pink in appearance to be used for subcutaneous (SC) injection. The test article was milled and supplied in an aqueous vehicle (see Table 1). The test article was filled into vials, stoppered, sealed and subjected to gamma sterilization at between 25-45 kGy.

TABLE 1

| Batch analysis | | |
|---|---|---|
| Polysorbate 20/tween 20 (% per mL formulated cabotegravir) | PEG3350 (% per mL formulation cabotegravir) | Mannitol (% per mL formulation cabotegravir) |
| 2.0 | 2.0 | 3.5 |

Twelve male Sprague-Dawley rats (body weight approximately 275-300 grams upon arrival), from Charles River Laboratories, Raleigh, were used in this study. Rats were randomized by number one day prior to the start of study. All rats were euthanized at study end.

Dose volumes administered for cabotegravir (target concentration of 200 mg/mL) were based on animal weights obtained just prior to dosing to achieve a target dosage of 10 mg/kg (groups 1 and 2) and 5 mg/kg (groups 3 and 4). Test article was resuspended prior to dosing by inverting supplied vials and checking vial bottom for non-resuspended sediments. Syringes used to dose cabotegravir were weighed pre- and post-dose to determine exact amount of cabotegravir administered. Rats were lightly anesthetized under isoflurane for a short period to perform the dosing procedure. Injection sites were shaved immediately prior to dosing, wiped with alcohol and allowed to dry. For groups 1 and 3, the cabotegravir doses were injected subcutaneously into the lower scapular region. After removing the dosing needle, minimal, but adequate, pressure was applied to the skin at the injection site (i.e., to keep the site still and closed) for approximately 1 minute to enable coagulation and sealing of the puncture. The sites were observed immediately after the needle was withdrawn to note any dose leakage. For groups 2 and 4, the rHuPH20 was injected subcutaneously first (approximately 3000 units in 100 μL, these syringes were not weighed), immediately followed by the Cabotegravir injection with the goal of injecting both formulations in the same subcutaneous space of the lower scapular region. After removing the second dosing needle, minimal, but adequate, pressure was applied to the skin at the injection site (i.e., to keep the site still and closed) for approximately 1 minute to enable coagulation and sealing of the puncture. Any dose leakage was noted. Injection sites were monitored daily for the first week of study and then weekly for the remainder of the study and observations recorded. Body weights were recorded on day 0 and then weekly for the remainder of the study.

Blood samples were collected via lateral vein or tail tip amputation. On study Day 0, following subcutaneous injection, blood samples (approximately 75 μL/rat/time point) were collected into 500 μL K2 EDTA tubes at 1, 2, 4 and 8 hr. Samples were then collected at 24 hrs., 48 hrs., and on Days 3, 7, 14, 21, 28, 56 and 84. Exactly 75 μL of whole blood was pipetted into a new tube containing 75 μL of sterile water. Samples were vortexed and placed on dry ice immediately. Samples were stored at −80° C. until transferred to Yinghe Li (DMPK, US) for analysis.

Rat blood: water samples were analyzed for cabotegravir using an analytical method based on protein precipitation, followed by UPLC/MS/MS analysis. The lower limit of quantification (LLQ) for cabotegravir was 5 ng/mL using a 150 μL aliquot of rat blood: water with a higher limit of quantification (HLQ) of 20000 ng/mL. Analyst software version 1.7.1 was used to acquire and process LC-MS/MS data. The applicable analytical runs met all predefined run acceptance criteria.

Pharmacokinetic analysis of cabotegravir blood concentration-time data was performed by a non-compartmental method using Phoenix WinNonlin®, Version 8.1 software. All computations utilized nominal sampling times and doses for the study. The area under the blood concentration-time curves (AUC) from the time of dosing to the last quantifiable timepoint (AUC0-t) was determined by WinNonlin® analysis using the linear trapezoidal linear interpolation rule. The maximum observed peak blood concentration (Cmax), and the time at which it was observed (Tmax) were determined by WinNonlin® analysis and by visual inspection of the data. Statistical analysis was limited to mean, median and standard deviation, as appropriate, and was performed using WinNonlin® analysis.

Individual and mean blood pharmacokinetic parameters of cabotegravir following subcutaneous administration at a target dose of 5 or 10 mg/kg with and without coadministration of rHuPH20 are presented in Table 2 below. The mean blood concentration-time with standard deviation curve is presented graphically in the FIGURE.

TABLE 2

Individual and mean blood pharmacokinetic parameters for cabotegravir following a single subcutaneous administration at a target Dose of 5 or 10 mg/kg with or without co-administration of rHuPH20

| Group/Dose | Animal ID | AUC (0-tlast) µg*h/mL | Cmax (ng/ml) | Tmax (h)[a] | T½ (h) |
|---|---|---|---|---|---|
| Group 1: Cabotegravir | 11 | 9970 | 12000 | 340 | 230 |
| (10 mg/kg) | 12 | 6333 | 5100 | 340 | 1100[b] |
| | 3 | 5644 | 7100 | 340 | 430 |
| Mean ± SD | | 7320 ± 2320 | 8000 ± 3500 | 340 [NA] | 330 ± 141 |
| Group 2: Cabotegravir | 4 | 6278 | 10000 | 340 | 210 |
| (10 mg/kg) and Halozyme | 7 | 7008 | 6800 | 340 | 360 |
| enzyme (rHuPH20) | 9 | 9916 | 10000 | 340 [NA] | 510 |
| Mean ± SD | | 7730 ± 1930 | 9100 ± 2100 | 340 | 360 ± 150 |
| Group 3: Cabotegravir | 10 | 4545 | 7600 | 340 | 200 |
| (5 mg/kg) | 2 | 5221 | 8000 | 170 | 220 |
| | 5 | 3432 | 5200 | 340 | 170 |
| Mean ± SD | | 4400 ± 903 | 7000 ± 1500 | 340 [170-340] | 200 ± 27 |
| Group 4: Cabotegravir | 1 | 3348 | 3200 | 340 | 240 |
| (5 mg/kg) and Halozyme | 6 | 1654 | 2600 | 340 | 160 |
| enzyme (rHuPH20) | 8 | 3397 | 5700 | 170 | 140 |
| Mean ± SD | | 2800 ± 993 | 3800 ± 1600 | 340 [170-340] | 180 ± 53 |

[a]Tmax reported as median and [range]

[b]Animal 12 extrapolated parameters (T½) excluded from mean ± SD due to AUC extrapolation >20% (30%)

Following a single subcutaneous injection of the cabotegravir suspension Sprague-Dawley rats at target doses of 5 and 10 mg/kg, systemic exposure as defined by AUC was approximately dose proportional. The systemic exposure of to the cabotegravir, generally was similar with and without administration of rHuPH20 (3000 U), with the respective mean half-life values of 360 and 330 hours (10 mg/kg CAB) and 180 and 200 hrs (5 mg/kg CAB).

Example 2

Safety and Pharmacokinetics of Cabotegravir Co-Administered with Recombinant Human Hyaluronidase PH20 (rHuPH20)

The safety and pharmacokinetics of a single administration of cabotegravir (CAB) 200 mg/mL (CAB200) and CAB 400 mg/mL (CAB400) subcutaneously (abdominal) co-administered with rHuPH20 has been evaluated in Cohort 4 h of an ongoing Phase I study in healthy adult volunteers (NCT04484337). Formulations of CAB200 and CAB400 are shown in Table 2. Safety results presented are based on data entered in participants' case report forms. The maximum severity of adverse events was graded according to the Division of AIDS Table for Grading the Severity of Adult and Pediatric Adverse Events, version 2.1, July 2017.

All 17 participants who received an injection in Cohort 4 h reported injection site reactions (ISRs), shown in Table 3. Among these, 14 (82%) injections led to Grade 1 (mild) or Grade 2 (moderate) ISRs, 3 (18%) participants developed Grade 3 (severe) erythema based on the surface areas of these ISRs. In most cases, symptoms caused no or minimal interference with participants' usual social & functional activities. No serious adverse events (SAEs) have been reported in Cohort 4 h. The local tolerability reactions were self-limited and consistent with the known safety profile of CAB and rHuPH20 individually, thus, showing that the addition of rHuPH20 to cabotegravir does not change the injection site reaction profile.

TABLE 3

CAB200 and CAB400 formulations

| Ingredients | CAB 400 mg/mL | CAB 200 mg/ml | Function |
|---|---|---|---|
| GSK1265744A, free acid | 400 | 200 | Active Substance |
| Polysorbate 20 | — | 20 | Wetting Agent |
| Poloxamer 338 | 38 | — | Wetting agent/ Stabilizer |
| Polyethylene Glycol 3350 | 35 | 20 | Stabilizer |
| Mannitol | 20 | 35 | Tonicity Agent |
| Water for Injection | q.s. | q.s. | Vehicle |

TABLE 4

| injection site reactions after dosing with Cabotegravir and rHuPH20 | Cohort 4 h 400 mg CAB [1 mL CAB400 or 2 mL CAB200] + rHuPH20 (n = 17) |
|---|---|
| Any AE, n (%) | 17 (100) |
| Drug-related AEs, n (%) | 17 (100) |
| Drug-related serious AEs, n (%) | 0 |
| Drug-related AEs leading to withdrawal, n (%) | 0 |
| Any ISR AE, n (% of injections) | 17 (100) |
| Grade 1 events, n (% of ISRs)† | 3 (18) |
| Grade 2 events, n (% of ISRs)† | 11 (65) |
| Grade 3 events, n (% of ISRs)† | 3 (18) |
| Any injection site pain/tenderness, n (% of injections) | 17 (100) |
| Grade 1 events, n (% of pain AEs) | 9 (53) |
| Grade 2 events, n (% of pain AEs) | 8 (47) |
| Grade 3 events, n (% of pain AEs) | 0 |
| Any injection site erythema, n (% of injections) | 17 (100) |
| Grade 1 events, n (% of erythema AEs) | 3 (18) |
| Grade 2 events, n (% of erythema AEs) | 11 (65) |
| Grade 3 events, n (% of erythema AEs) | 3 (18) |
| Any injection site nodule, n (% of injections) | 2 (12) |
| Grade 1 events, n (% of nodule AEs) | 0 |
| Grade 2 events, n (% of nodule AEs) | 2 (100) |
| Grade 3 events, n (% of nodule AEs) | 0 |
| Any injection site swelling/induration, n (% of injections) | 15 (88) |
| Grade 1 events, n (% of swelling AEs) | 6 (40) |
| Grade 2 events, n (% of swelling AEs) | 9 (60) |
| Grade 3 events, n (% of swelling AEs) | 0 |

†Maximum grade reported following the injection. The denominator is the total number of injections leading to ≥1 ISR. There were no Grade 4 or 5 ISRs

Example 3

Clinical Study

Clinical Modelling

The PPK model used for prediction was built based on a total of 23,926 CAB plasma concentrations collected from 1647 adult participants in 16 previous CAB studies. Based on rat PK data, it is concluded that one can assume that cabotegravir (CAB) PK is dose proportional and is similar with and without PH20. Under these assumptions, it is predicted by the population PK (PPK) model that 2000 mg Q3M (quarterly dosing) of CAB will result in CAB plasma concentrations above those observed in CAB Phase 3 studies that demonstrated efficacy and below the safety threshold of 22.5 μg/mL. This Cmax of 22.5 μg/mL was not associated with any toxicity. The median of CAB plasma concentrations following 2000 mg Q3M is predicted to stay below the safety threshold of 22.5 μg/mL.

Safety Summary

In a Phase 1 open-label, dose-escalation study to investigate the safety, tolerability and pharmacokinetics of single-dose administration of various CAB formulations with and without rHuPH20 in healthy adult participants, CAB200 at doses of 800, 1600 and 3200 mg have been administered with rHuPH20 (10,000 IU). rHuPH20 and CAB formulations were administered sequentially; subcutaneous (SC) administration by a health care provider (HCP) is via a butterfly needle and slow SC infusion in the abdominal SC tissue using a syringe pump.

CAB200 (Long-Acting, SC, PK) with rHuPH20

A summary of CAB200 LA SC PK data with rHuPH20 is set forth in the Table below.

In Study 212482, single SC injection of CAB200 (2 mL/400 mg) with rHuPH20 (5000 units) was studied in Cohort 4 h.

In Study 218012, single SC injection of CAB200 with rHuPH20 was studied in cohorts A1 (4 mL/800 mg CAB200), A2 (8 mL/1600 mg CAB200) and A3 (16 mL/3200 mg CAB200). The dose of rHuPH20 was 10000 units.

In both studies, rHuPH20 was injected first, followed by SC injection of CAB200.

TABLE 5

Baseline characteristics of participants receiving CAB400-D SC injections in Study 212482

| Study | Cohort | CAB200 dose | N[1] | Data cut | PH20 dose | Cmax |
|---|---|---|---|---|---|---|
| 212482 | 4 h | 400 mg (2 mL) | 8 (6) | W36 | 5000 units | 2.35 (1.79- |
| | A1 | 800 mg (4 mL) | 10 (6) | W24 | | 4.91 (2.34- |
| 218012 | A2 | 1600 mg (8 | 9 (3) | W20 | 10000 units | 8.35 (3.76- |
| | A3 | 3200 mg (16 | 2 (0) | W12 | | 16.25 (15.1- |

1. Number in Parenthesis Denotes Number of Females. 2. Median (Range)

CAB200 SC injections with rHuPH20 resulted in higher Cmax that was approximately twice has high as the simulated Cmax of CAB200 IM injections.CAB SC Cmax remained below the safety threshold of 22.5 μg/mL at a dose level of 3200 mg or lower. Four to 6 weeks after the injection, PK profiles between CAB200 SC injections with rHuPH20 and CAB200 IM injection (simulated) became similar. These observations were consistent across all dose levels. CAB200 SC PK with rHuPH20 is dose proportional at 400 mg-1600 mg (data up to 24 weeks post-injection).

Since modifications will be apparent to those of skill in the art, it is intended that the invention(s) are limited only by the scope of the appended claims.

The invention claimed is:

1. A combination, comprising a soluble hyaluronidase and a suspension comprising cabotegravir, wherein the soluble hyaluronidase and cabotegravir are co-formulated.

2. A kit, comprising the combination of claim 1.

* * * * *